(12) United States Patent
Turco

(10) Patent No.: US 9,963,514 B2
(45) Date of Patent: May 8, 2018

(54) BAG3 RECEPTOR BINDING MOLECULES FOR USE AS A MEDICAMENT

(71) Applicant: BIOUNIVERSA S.R.L., Fisciano (SA) (IT)

(72) Inventor: Maria Caterina Turco, Avellino (IT)

(73) Assignee: BIOUNIVERSA S.R.L., Fisciano (SA) (IT)

( * ) Notice: Subject to any disclaimer, the term of this patent is extended or adjusted under 35 U.S.C. 154(b) by 0 days. days.

(21) Appl. No.: 14/909,819

(22) PCT Filed: Jul. 23, 2014

(86) PCT No.: PCT/IB2014/063352
§ 371 (c)(1),
(2) Date: Feb. 3, 2016

(87) PCT Pub. No.: WO2015/019230
PCT Pub. Date: Feb. 12, 2015

(65) Prior Publication Data
US 2016/0168255 A1    Jun. 16, 2016

(30) Foreign Application Priority Data

Aug. 7, 2013 (IT) .............................. MI2013A1351

(51) Int. Cl.
| | | |
|---|---|---|
| *A61K 39/395* | (2006.01) | |
| *G01N 33/53* | (2006.01) | |
| *C07K 16/28* | (2006.01) | |
| *C07K 16/30* | (2006.01) | |
| *A61K 39/00* | (2006.01) | |

(52) U.S. Cl.
CPC .......... *C07K 16/2896* (2013.01); *C07K 16/28* (2013.01); *C07K 16/2863* (2013.01); *C07K 16/303* (2013.01); *A61K 2039/505* (2013.01); *A61K 2039/507* (2013.01); *C07K 2317/20* (2013.01); *C07K 2317/54* (2013.01); *C07K 2317/55* (2013.01); *C07K 2317/76* (2013.01)

(58) Field of Classification Search
None
See application file for complete search history.

(56) References Cited

FOREIGN PATENT DOCUMENTS

| EP | 1465927 B1 | 12/2011 |
|---|---|---|
| WO | 2003/055908 A2 | 7/2003 |
| WO | 2004/016643 A2 | 2/2004 |
| WO | 2007/056470 A2 | 5/2007 |
| WO | 2009/036149 A2 | 3/2009 |
| WO | 2011/067377 A1 | 6/2011 |
| WO | 2014/147503 A2 | 9/2014 |

OTHER PUBLICATIONS

Daniel-Carmi et al. (2009, Int. J. Cancer 125:2810-2819).*
Rosati et al., 2015, Nature Communications 6:8695, pp. 1-11.*
Mudhasani et al., "IFITM-2 and IFITM-3 but Not FITM-1 Restrict Rift Val ley Fever", Journal of Virology, May 29, 2013, 15 pages.
Siegrist et al., "The Small Interferon-Induced Transmembrane Genes and Proteins", Journal of Interferon & Cytokine Research, Aug. 11, 2010, 15 pages.
Huayuan et al., "BAG3: a new therapeutic target of human cancers?", Histology and Histopathology, Mar. 2012, 5 pages.
Andreu et al., "Identification of the IFITM family as a new molecular marker in human colorectal tumors", Cancer Prevention Research, American Association for Cancer Research, United States, Feb. 17, 2006, 7 pages.
Rosati et al., "Apoptosis inhibition in cancer cell s: A novel molecular pathway that involves BAG3 protein", International Journal of Biochemistry and Cell Biology, Pergamon, GB, Jul. 10, 2007, 6 pages.
Jarvis et al., "Small Molecule Inhibitors of the Neuropilin-1 Vascular Endothelial Growth Factor A (VEGF-A) Interaction", Journal of Medicinal Chemistry, Nov. 27, 2009, 12 pages.
Rosati et al., "Expression of the Antiapoptotic Protein BAG3 is a Feature of Pancreatic Adenocarcinoma and Its Overexpression is Associated With Poorer Survival", The American Journal of Pathology, Nov. 5, 2012, 6 pages.
Ammirante et al., "IKKy protein is a target of BAG3 regulatory activity in human tumor growth", Laboratory of Gene Regulation and Signal Transduction, Apr. 20, 2010, pp. 6.
Rosati et al., "Role of BAG3 protein in leukemia cell survival and response to therapy", Elsevier, Jun. 15, 2012, 5 pages.
Festa et al., "BAG3 Protein is Overexposed in Human Glioblastoma and is a Potential Target for Therapy", The American Journal of Pathology, Jun. 6, 2011, pages.
Franceschelli et al., "BAG2 Gene Expression is Regulated by Heat Shock Factor 1", Journal of Cellular Physiology, Oct. 21, 2007, 3 pages.
Hoelder et al., "Discovery of small molecule cancer drugs: Successes, challenges and opportunities", Elsevier, Mar. 3, 2012, 22 pages.
Ulbricht et al., "Cellular Mechanotransduction Relies on Tension-Induced and Chaperone-Assisted Autophagy", Medical College of Wisconsin, Milwaukee, Mar. 4, 2013, 30 pages.
Marco et al., "Detection of soluble BAG3 and anti-BAG3 antibodies in patients with chronic heart failure", www.nature.com/cddis, Feb. 14, 2013, 2 pages.
International Search Report for Application PCT/IB2014/063352, dated Nov. 21, 2014.

* cited by examiner

*Primary Examiner* — Elizabeth C. Kemmerer
(74) *Attorney, Agent, or Firm* — Perkins Coie LLP; Viola T. Kung

(57) ABSTRACT

The present invention relates to the use of BAG3 receptor-binding molecules as a medicament, in particular for use in the treatment of diseases of an immune, inflammatory, cardiovascular, neoplastic and/or degenerative nature.

17 Claims, 13 Drawing Sheets

Fig. 8
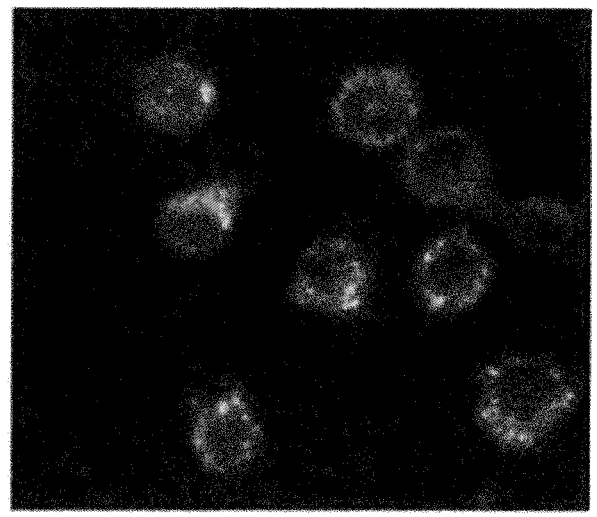
rBAG3-FITC
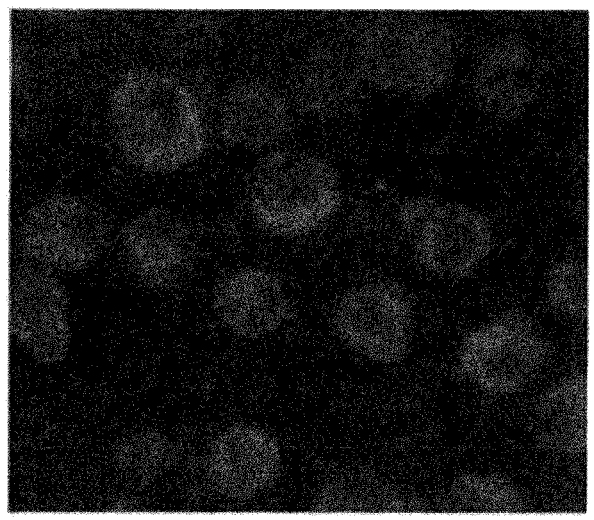
BSA-FITC

BAG3 RECEPTOR BINDING MOLECULES FOR USE AS A MEDICAMENT

This application is a National Stage of International Application PCT/IB2014/063352, filed Jul. 23, 2014, published Feb. 12, 2015, under PCT Article 21(2) in English; which claims the priority of Italian Application No. MI2013A001351, filed Aug. 7, 2013. The contents of the above-identified applications are incorporated herein by reference in their entireties.

BACKGROUND ART

BAG3, a 74 kDa cytoplasmic protein, belongs to the family of co-chaperonins that interact with the ATPase domain of the protein HSP70 (Heat Shock Protein 70) through the structural domain known as the BAG domain. Furthermore, BAG3 protein contains a WW domain (Trp-Trp), a proline-rich region (PXXP), and two conserved motifs IPV (Ile-Pro-Val), which can mediate binding to other proteins. Thanks to the nature of BAG3 protein as an adapter (attributable to the presence of many functional domains), such protein can therefore interact with different proteins. In humans, bag3 gene expression is constitutive in few kinds of normal cells, including myocytes, while mutations thereof are associated with diseases of the skeletal and cardiac muscles. Moreover, BAG3 protein is expressed in many types of primary tumours or tumour cell lines (lymphoid or myeloid leukemias, neuroblastoma, pancreatic cancer, thyroid cancer, breast and prostate cancer, melanoma, osteosarcoma, and glioblastoma, and tumours of the kidney, colon, and ovary). In normal cell types, such as leukocytes, epithelial and glial cells and cells of the retina, bag3 gene expression can be induced by stressing agents, such as oxidants, high temperatures, lack of serum, heavy metals, HIV-1 infections, etc. These data indicate that bag3 gene expression regulation is an important component in the cellular response to stress and is correlated with the presence of elements that respond to HSF1 (Heat Shock Transcription Factor 1), which is activated in various forms of cell stress in the BAG3 gene promoter (Franceschelli S., et al. J Cell Physiol 215 (2008) 575-577).

Moreover, due to the presence of many protein-protein interaction domains in the structure thereof, BAG3 protein influences cell survival in different types of cells, interacting with different molecular partners. (A. Rosati et al. Biochim Biophys Acta. 2012; 1826:365-9).

The first mechanism reported in relation to BAG3 anti-apoptotic activity was identified in osteosarcoma and melanoma cells, where it was observed that BAG3 protein modulates the activation of transcription factor NF-kB and cell survival (Ammirante M. et al., Proc Natl Acad Sci USA 107 (2010) 7497-7502). A different molecular mechanism has been described in glioblastoma cells, where BAG3 protein cooperates in a positive way with HSP70 protein to maintain BAX protein in the cytosol and prevent the translocation thereof into the mitochondria (Festa M. et al., Am J Pathol 178 (2011) 2504-25). Finally, in some tumours, BAG3 has been shown to regulate proteins that modulate cell adhesion.

The presence of cytoplasmic BAG3 protein has also been described in many different cellular systems and has been associated, not only with various tumours, but also in diseases in general related to cell survival.

It has recently been demonstrated that BAG3 protein can be secreted by certain cells, in particular by pancreatic adenocarcinoma cells and by cardiomyocytes when subjected to an oxidative stress. (Rosati et al., Am J Pathol. 2012 November; 181(5):1524-9; De Marco et al. Cell Death Dis. 2013; 4:e495.). Patent application n. WO2011/067377 describes soluble BAG3 protein, i.e. the said protein when it is secreted by the cells, as a biochemical marker in serum which is highly specific for the diagnosis of certain pathological conditions, such as cardiac diseases and tumour of the pancreas. In particular, it has been demonstrated that, in patients suffering from pancreatic adenocarcinoma, the soluble BAG3 concentration is generally higher than 10 ng/ml, significantly higher than in the serum of healthy individuals. Furthermore, it has recently been reported that BAG3 protein is expressed in 346/346 patients with pancreatic ductal adenocarcinoma (PDAC) and is released by the cells of the tumour of the pancreas, but such protein is not expressed in either the surrounding non-neoplastic tissues or in a normal pancreas; likewise, it has been reported that the levels of expression of BAG3 are related to patient survival. In particular, it has been demonstrated that the BAG3 protein secreted by tumour cells in the pancreas induces the activation of macrophages and the production, thereby, of molecules that support neoplastic growth and, in the heart, are responsible, after an ischemic event, for the phagocytosis of the damaged myocytes and for the replacement of the necrotic myocardium with scar tissue and the consequent tissue remodelling.

Patent application n. MI2013A000403 also describes how the inhibition of the BAG3 protein through the use of monoclonal anti-BAG3 antibodies impairs development of pancreatic tumours. Indeed, by interfering with the binding of BAG3 to macrophages, through a monoclonal anti-BAG3 antibody, the activation of macrophages and tumour growth is inhibited. Treatment with anti-BAG3 antibodies represents a new, more effective therapeutic tool for the management of tumours of the pancreas.

As is known, conventional chemotherapy treatments for tumour diseases, as well as treatments of inflammatory and immune diseases with corticosteroids or NSAIDs (non-steroidal anti-inflammatory drugs) pose numerous drawbacks linked to side effects and are not, at present, definitive means of managing such diseases.

There is, therefore, an evident need for a new and improved therapeutic treatment which has the advantage of being highly specific and having few or indeed no side effects, as compared with the conventional, commonly known therapies used for the management of the diseases of an immune, inflammatory, cardiac and neoplastic nature described in the present invention.

DISCLOSURE OF INVENTION

Subsequent studies have identified membrane receptors expressed on macrophages, which are responsible for binding the BAG3 protein to the surface thereof and for the activation thereof. Through this identification, BAG3 receptor-binding molecules, such as small molecules, peptides, polypeptides, antibodies and/or fragments thereof, can be designed which interfere specifically with the binding between the BAG3 protein and the receptor thereof.

Such selective blocking of the BAG3 ligand to the receptor thereof, therefore allows a greater effectiveness to be obtained in the treatment of the target cells and greater specificity, which brings with it a reduction in side effects of conventional non-specific treatments.

It was therefore surprisingly demonstrated, for the first time, that the inhibition of the binding of the BAG3 protein to the membrane receptors thereof present on the surface of target cells, through the use of BAG3 receptor-binding molecules, inhibits the activation of macrophages and that this process is responsible for the positive effect of BAG3 on neoplastic growth.

Treatment with the BAG3 receptor-binding molecules therefore represents a new and improved therapeutic tool for the management of neoplastic diseases, as well as other diseases linked to the activation of macrophages, such as diseases of an inflammatory, immune, cardiac, and degenerative nature.

The specific receptor for the BAG3 protein identified through the studies described by the inventors hereof is composed of two proteins, namely IFITM-2 (Interferon-induced transmembrane protein 2) and NRP-1 (Neuropilin-1).

IFITM2 has been described as a membrane protein which is induced by Interferon and involved in the regulation of viral infection. Until this time, the role thereof as receptor for physiological ligands was unknown. The extra-cellular portion of IFTM-2 contains a proline-rich motif of the PPxY type (UniProt accession number for human IFTM-2: Q01629; sequence from aa 16 to aa 19 PPNY), which is stated as a site with particularly binding affinity with the BAG3 WW domain (Ulbricht A. et al. Curr Biol. 2013; 23(5):430-5).

Furthermore, when researching other putative domains of the extra-cellular portion of IFITM-2, two SH3 domains were identified (www.expasy.org). SH3 domains have been identified as potential interactors of the proline-rich domains of BAG3 protein (A. Rosati et al. Biochim Biophys Acta., 2012; 1826:365-9)

NRP-1 (Neuropilin-1) is non-specific chain (co-receptor) of various types of receptors, such as receptors for class 3 semaphorin, receptors for members of the VEGF family (VEGF-A, B, C, D, and E), transforming growth factor β1 (TGF-β1), hepatocyte growth factor (HG), platelet-derived growth factor (PDGF), and fibroblast growth factors (FGFs). In these receptors, NRP-1 participates in binding and amplifies signal transduction.

It was shown in WO2009/036149 that when the VEGF-B protein binds to the VEGFR-1 receptor and to the co-receptor thereof, NRP-1 acts as an inhibitor of apoptosis in the retina and in the brain.

It has also been described that blocking the binding of the VEGF-A protein to the NRP-1 co-receptor attenuates phosphorylation of the VEGFR2 receptor and migration of endothelial cells (Jarvis A et al., J. of Medicinal Chemistry 53, p. 2215-2226 (2010). Therefore, depending on the receptor with which it interacts, the NRP-1 co-receptor plays a versatile role in angiogenesis, axon guidance, cell survival, apoptosis, migration and in cell invasion.

In particular, in the event that NRP-1 shows co-receptor activity in relation to IFITM-2 through the signal activated by the extra-cellular BAG3 protein, induction of the release of IL-6 is observed in macrophages, together with increased levels of proteins connected to the activation of the inflammatory process, such as iNOS and COX-2.

Therefore, treatment with any molecule able to inhibit, specifically, the binding of the BAG3 protein to the macrophages through a specific interaction with the BAG3 receptor proves particularly effective in the treatment of those diseases characterised by the activation of macrophages, such as neoplastic diseases and diseases of an inflammatory, immune, cardiac, or degenerative nature. Indeed, these BAG3 receptor-binding molecules are able to both bind and block the BAG3 protein binding to the receptor expressed by macrophages in a highly selective and targeted manner, and therefore to impede the pathological effects related to the BAG3 protein.

In particular, the use of the aforesaid BAG3 receptor-binding molecules in this treatment has the surprising advantage of being more specific for selected disease states characterised by the over-expression and release of BAG3 protein, and also less damaging in terms of side effects.

One embodiment of the present invention is therefore the use of BAG3 receptor-binding molecules as a medicament.

A further embodiment of the present invention is therefore to use BAG3 receptor-binding molecules expressed on the surface of the macrophages as a medicament. According to one aspect of the present invention, said BAG3 receptor-binding molecules bind to the IFITM-2 protein, the NRP-1 protein or both; according to a preferred aspect, such binding molecules bind to the IFITM-2 protein.

Said BAG3 receptor-binding molecules usable in accordance with the present invention can be small molecules, peptides, polypeptides, antibodies and/or fragments thereof. According to a preferred aspect of the present invention, said molecules BAG3 receptor-binding molecules are characterised by the fact that such molecules are not VEGF family proteins.

Still more preferably, said BAG3 receptor-binding molecules can be polyclonal or monoclonal antibodies, mouse antibodies, humanised antibodies, chimeric antibodies, recombinant antibodies, conjugated antibodies, scFv fragments (diabody, triabody and tetrabody), Fab fragments, and F(ab')2 fragments.

In a preferred aspect of the invention, said antibodies can be chosen from specific BAG3 receptor antibodies, preferably anti-IFITM-2 antibodies or anti-NRP-1 antibodies, and more preferably anti-IFITM-2 antibodies.

The term "small molecules" refers to a series of small biologically active molecules with low molecular weight, such as molecules identified for high throughput screening of combinatorial libraries, antibody fragments, peptides, chemically modified peptides, organic molecules, oligomers, and fragments of nucleic acids (e.g. RNAi), which have a therapeutic function as they are capable of binding to an appropriately identified specific pathological target. Some examples of small molecules are the known epidermal growth factor receptor (EGFR) inhibitors Gefitinib and Erlotinib, which inhibit EGFR in patients with tumours of the lung, or monoclonal anti-ERBB2 antibody Trastuzumab, which is used in the management of ERBB2-positive tumours of the breast, and numerous other examples (Hoelder S et al., Molecular Oncology 6, p. 155-176 (2012). One example of identification of a ligand-specific small molecule for the receptor of VEGF-A NRP1 is described in literature (Jarvis A et al., J of Medicinal Chemistry 53, p. 2215-2226 (2010).

The term "polyclonal antibody" refers to a mixture of antibodies which are genetically different since produced by different plasma cells and which recognise a different epitope of the same antigen.

The term "monoclonal antibody" refers to a set of antibodies which are all identical since produced by cell lines from only one type of immune cell (i.e. a cell clone).

The term "humanized antibody" refers to an antibody of human origin, whose hypervariable region has been replaced by the homologous region of non-human monoclonal antibodies.

The term "chimeric antibody" refers to an antibody containing portions derived from different antibodies.

The term "recombinant antibody" refers to an antibody obtained using recombinant DNA methods.

The term "conjugated antibody" refers to antibodies conjugated with drugs, toxins, radioactive substances or other agents.

The term "scFv fragment" (single chain variable fragment) refers to immunoglobulin fragments only capable of binding with the antigen concerned. ScFv fragments can also be synthesised into dimers (diabodies), trimers (triabodies) and tetramers (tetrabodies) using peptide linkers.

The terms "Fab fragment" (fragment antigen-binding) and "Fab2 fragment" refer to immunoglobulin fragments consisting of a light chain linked to the Fc fragment of the adjacent heavy chain, and such fragments are monovalent antibodies. When the Fab portions are in pairs, the fragment is called Fab2.

A further object of the present invention is the use the aforesaid BAG3 receptor-binding molecules in the treatment of a particular disease state which involves the activation of macrophages. Such disease state can be selected from: neoplastic diseases, inflammatory diseases, cardiac diseases, immune diseases, or degenerative diseases. Preferably, said neoplastic diseases can be selected from pancreatic cancer.

Preferably, said inflammatory diseases can be selected from diseases relating to inflammation of the skin, nerves, bones, blood vessels, and connective tissues, and more preferably, psoriasis, arthritis, neuritis, connectivitis.

Preferably, said cardiac diseases can be chosen from angina pectoris, myocardial infarction, ischemia, acute coronary syndrome, and acute and chronic cardiac failure. Preferably, said immune diseases can be chosen from autoimmune diseases such as rheumatic diseases, connective tissue diseases, neuromuscular diseases, endocrine diseases, gastrointestinal diseases, blood diseases, skin diseases, and vasculitis, and more preferably, rheumatoid arthritis, multiple sclerosis, connectivitis, lupus erythematosus, endometriosis, and ulcerative colitis. Preferably, said degenerative diseases can be chosen from neurodegenerative diseases and muscular degenerative diseases, and more preferably Alzheimer's disease, Parkinson's disease, and muscular dystrophy.

A further object of the present invention is the use of the aforesaid BAG3 receptor-binding molecules, in association with at least one anti-BAG3 antibody, as a combined preparation for simultaneous, separate, or sequential use.

According to a preferred embodiment of the invention, the aforesaid BAG3 receptor-binding molecules in association with at least one anti-BAG3 antibody, are used in the treatment of neoplastic diseases, inflammatory diseases, cardiac diseases, immune diseases or degenerative diseases.

In one aspect of the present invention, said BAG3 receptor-binding molecules can be administered to humans.

A further aspect of the present invention is to achieve a pharmaceutical composition comprising at least one BAG3 receptor-binding molecule in association with at least one pharmaceutically acceptable excipient.

A further object of the present invention is to achieve a pharmaceutical composition containing at least one BAG3 receptor-binding molecule and at least one anti-BAG3 antibody as a combined preparation for simultaneous, separate, or sequential use.

A further object of the present invention is the use of said composition as a medicament. A preferred embodiment of the present invention is the use of the aforesaid composition in the treatment of neoplastic diseases, inflammatory diseases, cardiac diseases, immune diseases or degenerative diseases.

The composition of the present invention can be formulated in a form suitable for oral administration or in a form suitable for parenteral or topical administration.

In a preferred embodiment of the present invention, said oral form can be selected from tablets, capsules, solutions, suspensions, granules, and oily capsules.

In a further preferred embodiment of the present invention, said topical form can be selected from cream, ointment, salve, solution, suspension, eye drops, pessary, nebuliser solution, spray, powder, or gel.

In a further preferred embodiment of the present invention, said parenteral form is selected from an aqueous buffer solution or an oily suspension.

Said parenteral administration can be selected from intramuscular, intravenous, intradermal, subcutaneous, intraperitoneal, intranodal, or intrasplenic administration. Said pharmaceutical composition can be administered to humans.

The following examples are intended merely to allow better understanding of the invention without in any way limiting it.

Legend. FT sample not bound to the resin; W5-1 W5-2 wash fractions with 5 mM imidazole. W10-1 W10-2 W10-3 wash fractions with 10 mM imidazole; E250-1, E250-2, E250-3 elution fractions with 250 mM imidazole. The results were obtained through an anti-penta His antibody conjugated to HRP used to highlight the presence of BAG3 recombinant protein.

Figure 3:
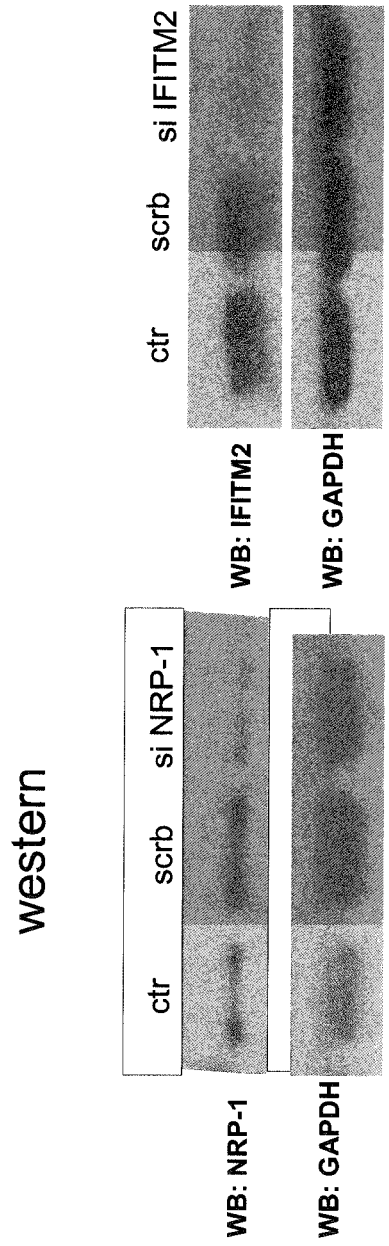

FIG. 3. Levels of NRP-1 and IFITM-2 were measured with the Western Blot technique in J774 control cells, transfected with a non-specific siRNA (scrb) or with an NRP-1- or 2-IFITM-specific siRNA.

Figure 4:
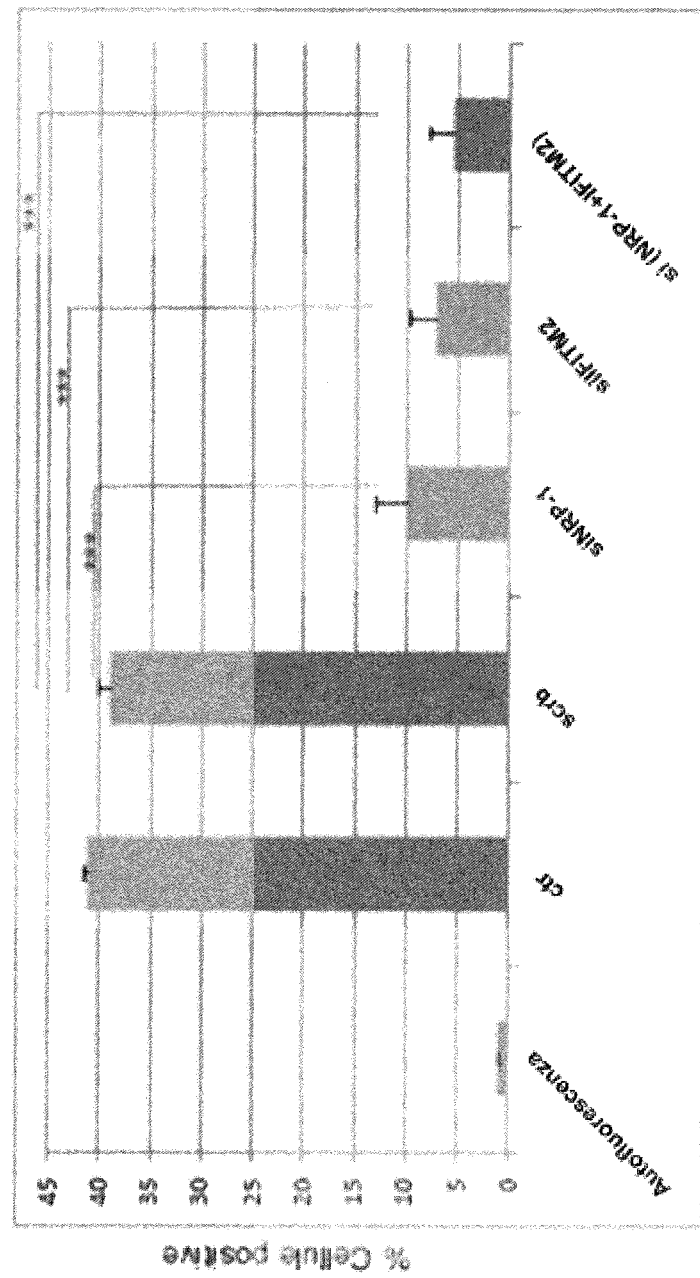

FIG. 4. The graphs show the percentage of fluorescence-positive cells obtained by flow cytometry from cells incubated with BAG3 recombinant protein bound to FITC. The ctr and scrb samples represent the percentage of control cells or cells transfected with a non-specific siRNA (scrb) which is bound by recombinant BAG3. This percentage decreased following transfection with NRP-1- or IFITM-2-specific siRNAs or with the two co-transfected siRNAs. The bars show the percentage of cells which showed positive for binding with BAG3 bound to FITC+standard deviation. *** $p<0.001$ VS scrb.

Figure 5:
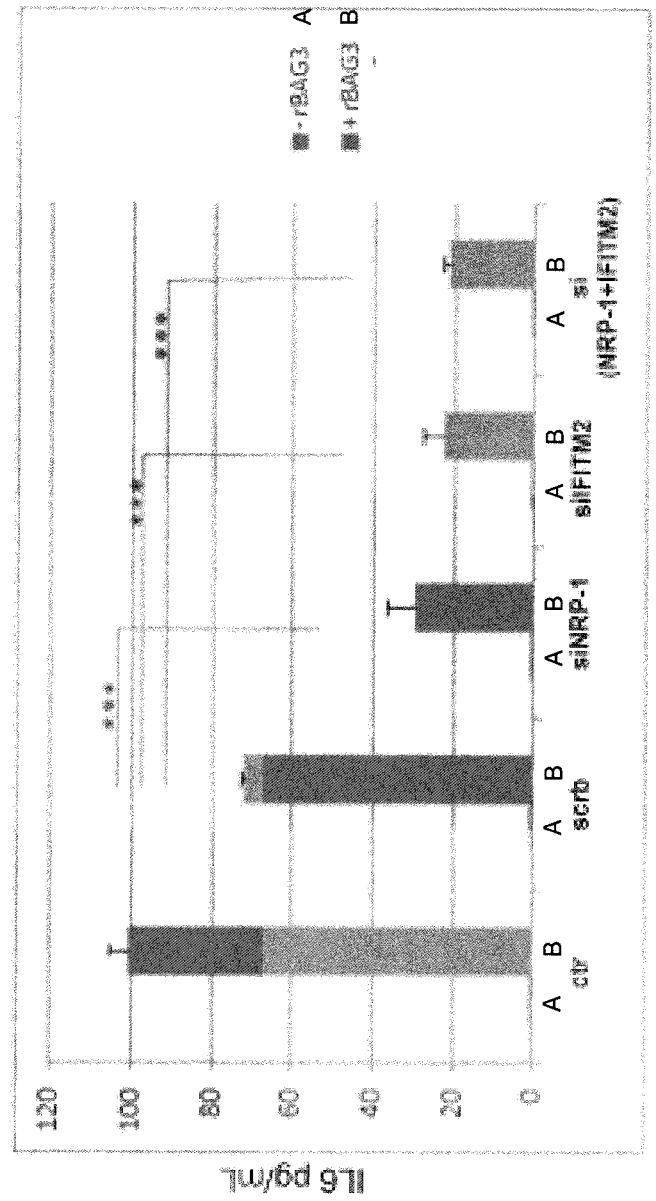

FIG. 5. The graphs show that the down-modulation of the membrane receptors, the NRP-1, IFITM-2, or both leads to a drastic decrease in the release of IL6, following stimulation with rBAG3 protein.

Figure 6:
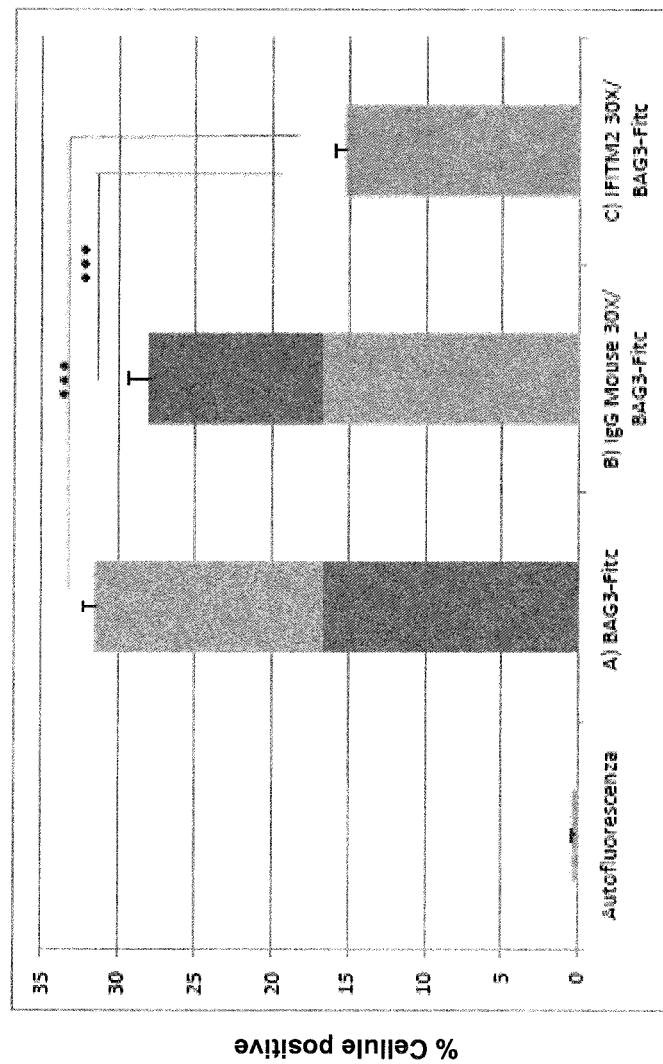

FIG. 6. The graph shows that the presence of the IFITM-2 antibody (Code H00010581M14 Novus Biologicals, Littleton, Colo., USA) leads to a 53.4% decrease in the binding of BAG3-FITC to the cell surface (C). ***$p<0.001$.

Figure 7:
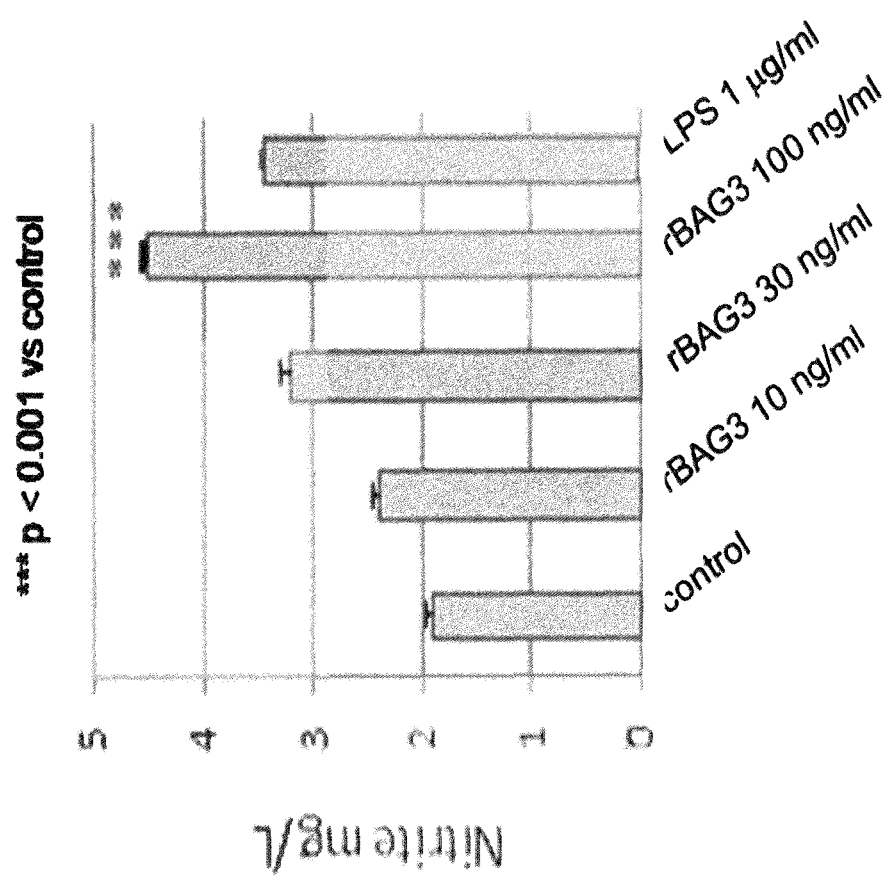

FIG. 7. The graph in the figure shows that, at a concentration of 100 ng/ml, the recombinant protein increases nitrite production by 200% compared to the control ($p<0.001$) and that the activity thereof is dose-dependent.

FIG. 8. The fluorescence microscopy images demonstrate the binding of the BAG3 protein to the cell surface of J774 cells through conjugation of the recombinant protein with a fluorophore.

Figure 9:
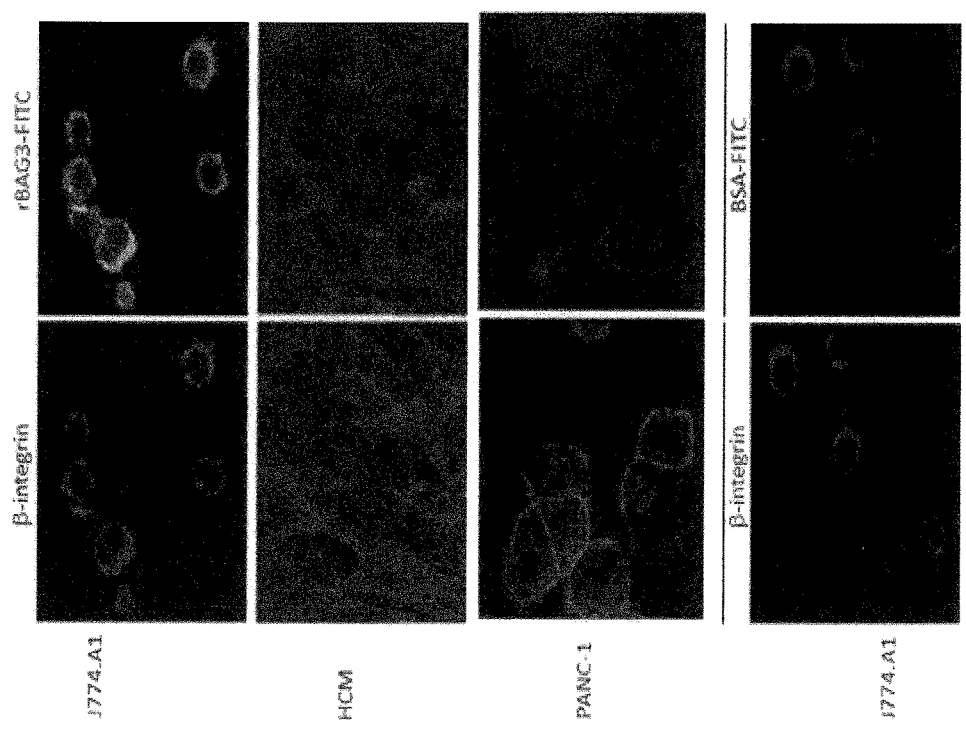

FIG. 9. The fluorescence microscopy images demonstrate that BAG3 protein binds the surface of macrophages and not heart muscle cells (HCM) or pancreatic adenocarcinoma cells (PANC-1)

Figure 10:
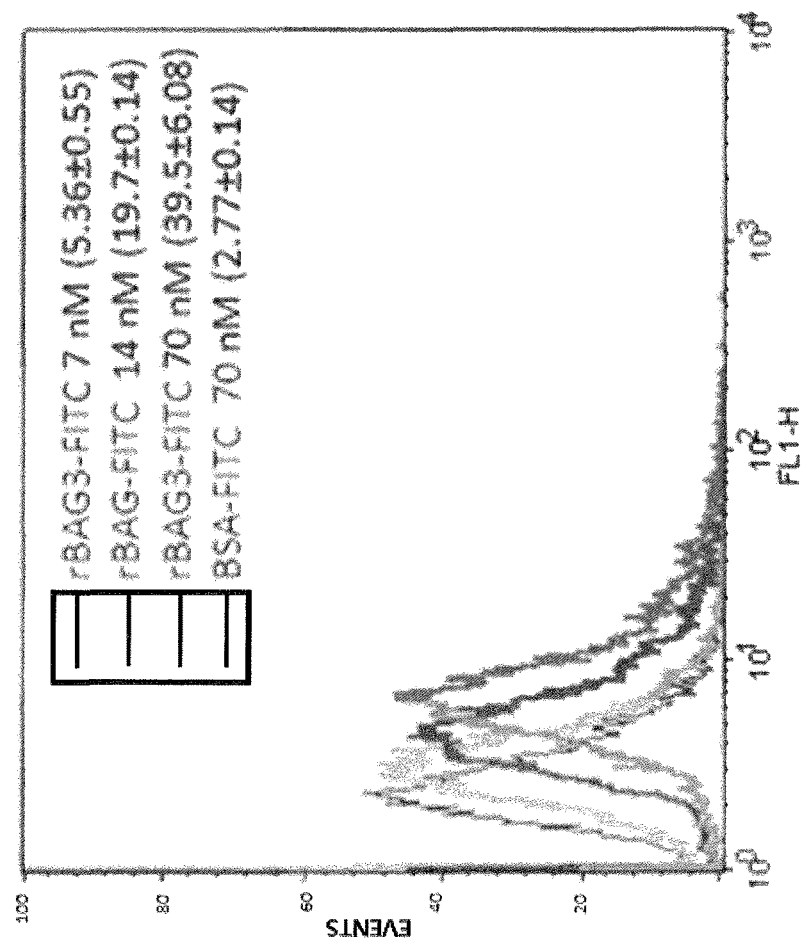

FIG. 10. Through flow cytometry analysis, it was observed that the FITC-BAG3 binds the macrophages of the J774 cell line.

Figure 11:
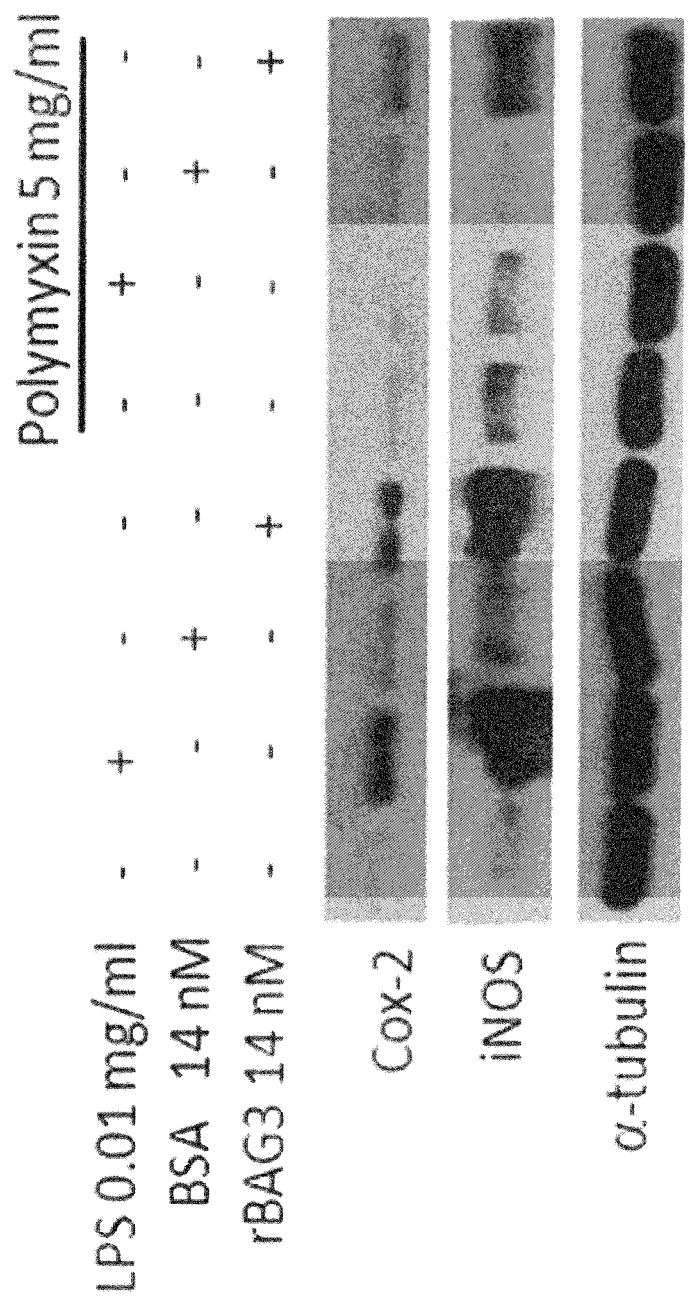

FIG. 11. It can be observed in the figure that COX-2 and iNOS enzyme levels increased following treatment of cells with rBAG3.

Figure 12:
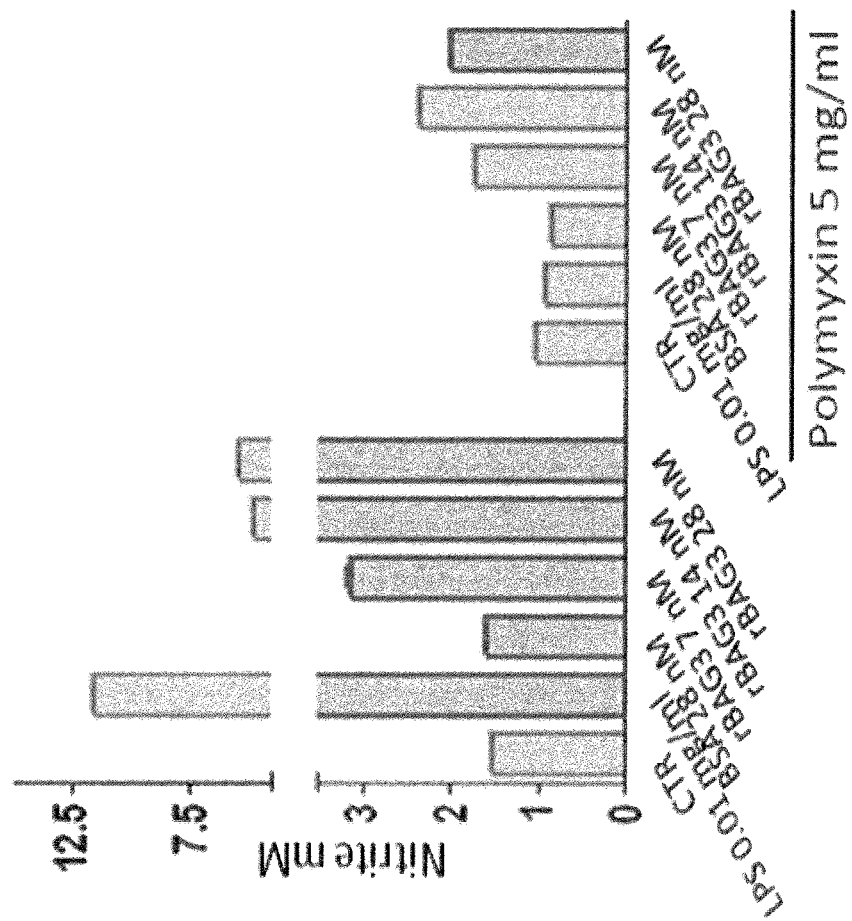

FIG. 12. It can be observed in the figure that BAG3 induces the release of nitrite, confirming that the macrophages were activated in response to the binding with the protein.

Figure 13:
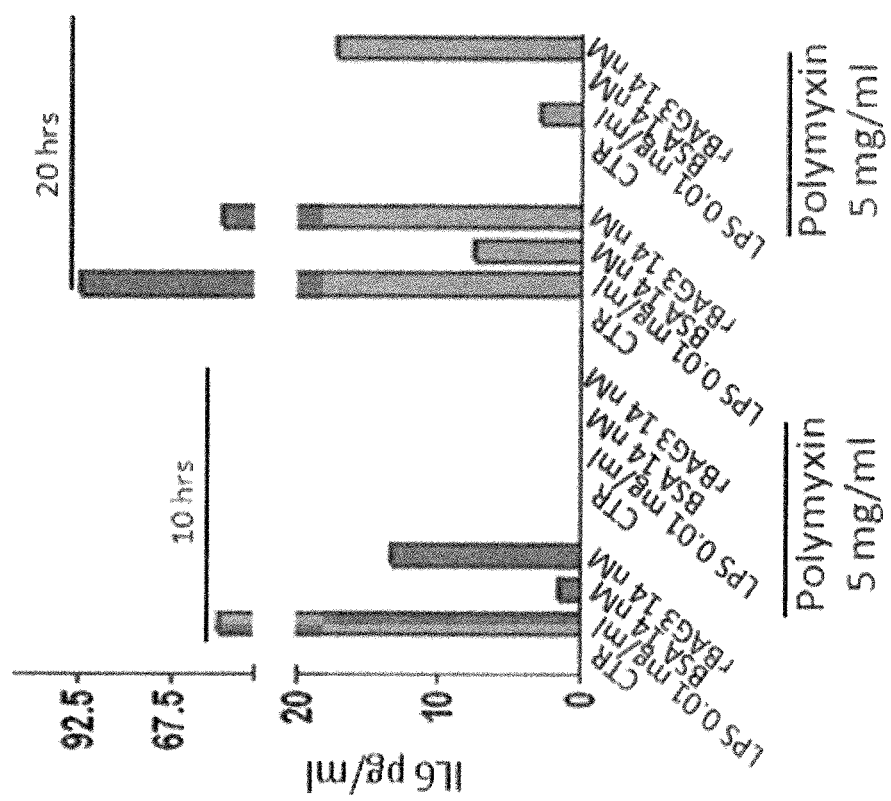

FIG. 13. This figure demonstrates that BAG3 induces the release of interleukin-6 (IL-6), confirming that the macrophages were activated in response to the binding with the protein.

EXAMPLES

Example 1. Fractionation of Membranes, Extraction and Solubilization of Complexes Containing BAG3 Recombinant Protein (rBAG3)

Two pools of 20 million macrophage cells (J774 cell line) were thawed on ice for 30 minutes. The cells were washed 3 times in 10 ml of cold PBS 1×, containing a solution of 1× protease inhibitors (PIC 1×, Roche) at pH 8.0. The cells were then re-suspended in 25 ml 1×PBS and incubated with 25 µg BAG3 recombinant protein (1 µg/ml) for one hour at 4° C. The sample of cells used for the negative control was incubated in the same conditions without the BAG3 recombinant protein. The cells were subsequently washed 3 times in 10 ml cold PBS 1× to remove the protein in excess. The final pellets were resuspended in 5 ml PBS 1×, PIC 1×, pH 8.0, and lysed mechanically on ice using a Dounce. The membranes were fractionated by sequential centrifugations as follows: 500 g for 5 min at 4° C., 15,000 g for 30 minutes at 4° C., and 100,000 g for one hour at 4° C. The plasma membrane fraction (pellets obtained after centrifugation at 100,000 g) was resuspended with 200 µl PBS 1×, PIC 1×, pH 8.0 and solubilized.

Figure 1:
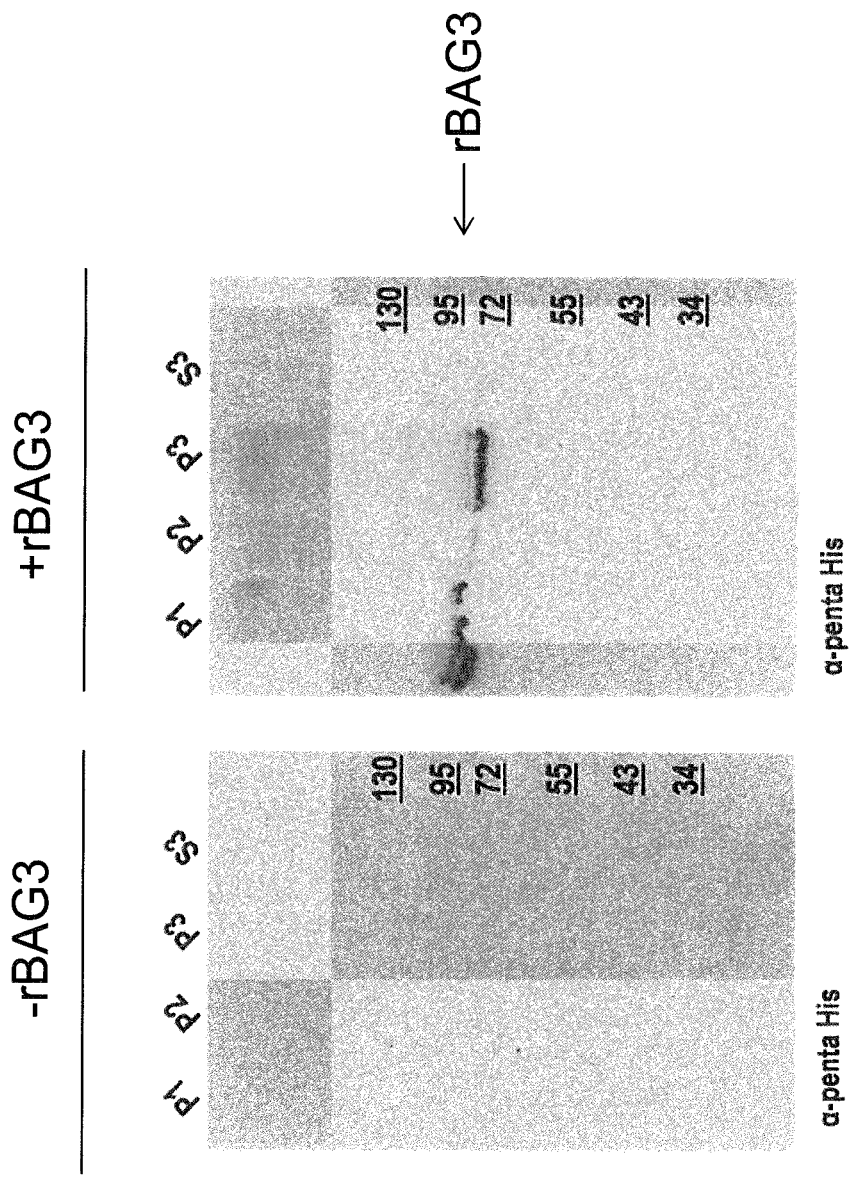
FIG. 1. P1: pellets after centrifugation at 500 g (whole cells); P2: pellets after centrifugation at 15,000 g (ER, mitochondria, nuclei); P3: pellets after centrifugation at 100,000 g (plasma membranes); S3: supernatants after centrifugation at 100,000 g. The results were obtained through an anti-penta His antibody conjugated to HRP, which was used to highlight the presence of BAG3 recombinant protein.

The samples were centrifuged at 100,000 g for one hour at 4° C. The pellets and supernatants were denatured with 2% SDS. The proteins were separated with SDS-PAGE and immobilized on PVDF membrane. An anti-penta His antibody conjugated to HRP was used to highlight the presence of BAG3 recombinant protein containing this tag type. FIG. 1 confirms that the rBAG3 recombinant protein is capable of binding to protein partners present on the plasma membrane.

Example 2. Purification of Complexes Containing BAG3 Recombinant Protein (rBAG3) Through Affinity Chromatography The proteins obtained from the fraction of the plasma membrane were diluted by the addition of 200 µl of solution containing 0.2% DDM, PBS 1×, PIC 1×, at pH 8.0 and dialyzed in a Slide-A-Lyzer dialysis cassette (10,000 MWCO, 0.1-0.5 ml capacity, Pierce) in 400 ml dialysis buffer (0.1% DDM, PBS 1×, PIC 1×, 5 mM imidazole, pH 8.0) for 1 h at 4° C. After changing the buffer, the dialysis was performed overnight. 25 µl Ni-NTA resin equilibrated in binding buffer (0.1% DDM, PBS 1×, PIC 1×, 5 mM imidazole at pH 8.0) were added to the dialyzed samples and incubated with agitation at 4° C. After centrifugation at 1000 g for 10 seconds, the supernatants were removed. The resins were washed twice with 4 volumes of binding buffer (100 µl) and washed three times with 4 volumes of washing buffer (0.1% DDM, PBS 1×, PIC 1×, 10 mM imidazole, at pH 8.0). The bound proteins were eluted with 3×2 volumes (50 µl) of elution buffer (0.1% DDM, PBS 1×, PIC 1×, 250 mM imidazole, at pH 8.0). Each fraction obtained from the purification was analyzed with SDS-PAGE and subsequently transferred onto PVDF membrane, followed by immunodetection with an anti-penta His antibody conjugated to HRP. The second fractions eluted were grouped together and concentrated with trichloroacetic acid (TCA). The proteins were precipitated for 2 hours on ice with cold 20% TCA. After centrifugation the pellets were washed thoroughly 3 times with cold acetone. The final pellets were re-suspended with 5 µl guanidine 8 M, Tris-HCl 100 mM, pH 8.0. This buffer allows solubilization of all the precipitated proteins and is compatible with mass spectrometry analysis. The protein concentration was determined by measuring absorbance at 280 nm with a Nanodrop 2000 spectrophotometer (ThermoScientific).

Figure 2:
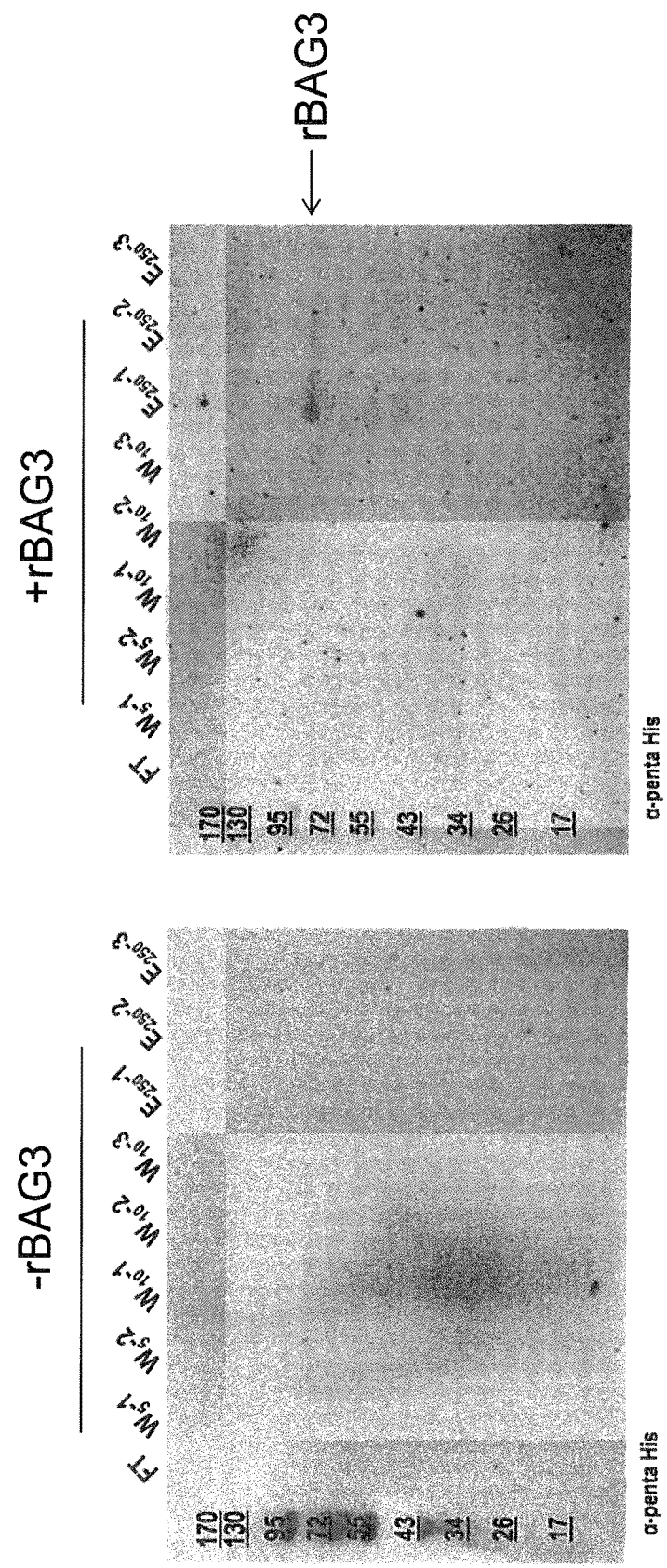
FIG. 2 shows that, in the absence of treatment of the J774 cells with the BAG3 recombinant protein, no protein is detected using an anti-His antibody. The purification of the recombinant protein complexes containing BAG3 from the solubilised plasma membranes prepared after incubation of rBAG3 with the J774 cells shows that the presence of rBAG3 was not observed in the rejected sample (FT) and likewise in the wash fractions. This confirms the specific rBAG3 binding to Ni-NTA resin and that the stringency of the washing buffers ensures the specificity of binding, as well as that the rBAG3 is completely eluted in the first two fractions with the 250 mM imidazole solution. The total proteins obtained in the elution fractions were determined after precipitation with TCA.

FIG. 2 shows that, in the absence of treatment of the J774 cells with the BAG3 recombinant protein, no protein is detected using an anti-His antibody. The purification of the recombinant protein complexes containing BAG3 from the solubilised plasma membranes prepared after incubation of rBAG3 with the J774 cells shows that the presence of rBAG3 was not observed in the rejected sample (FT) and likewise in the wash fractions. This confirms the specific rBAG3 binding to Ni-NTA resin and that the stringency of the washing buffers ensures the specificity of binding, as well as that the rBAG3 is completely eluted in the first two fractions with the 250 mM imidazole solution. The total proteins obtained in the elution fractions were determined after precipitation with TCA.

Example 3. LC-MSMS Analysis of the Complexes Containing the BAG3 Recombinant Protein After reduction with 15 mM DTT for 45 minutes at 55° C., 3.5 µg sample was alkylated with 50 mM iodoacetamide for 45 minutes at room temperature. Trypsin digestion was performed for 18 hours at 37° C. The sample was then dried with a Speed-Vac and finally resuspended in 10 ml 0.3% TFA. The samples were subjected to digestion after being pre-concentrated using a C18 capillary column Acclaim Pep Map 100 (5 micron, 100 A, 300 µm×5 cm, Dionex) with a solution containing 0.05% TFA, 98/2 H2O/ACN. The peptides were then separated using a C18 Acclaim PepMap100

(3 µm, 100 A, 75 µm×15 cm, Dionex) with a 0.1% formic acid buffer 10/80 H2O/ACN, 0.1%. The Tandem Mass Spectrometry (MSMS) was performed with a LTQ Velos (Thermo Scientific). The data were analyzed with Proteome Discoverer 1.1 (MASCOTTE algorithm, v2.2.4) software, using the Swiss-Prot database (UniProtKB, v12/2012). Table 1 shows the plasma membrane proteins co-purified in complex with rBAG3. In particular, such membranes included two receptor molecules: Interferon-induced transmembrane protein 2 (IFITM-2) and neuropilin-1 (NRP-1). For the first time, therefore, receptors of the BAG3 plasma membrane have been identified through a proteomic approach. Through this process, 9 new BAG3 partners have been identified including 2 receptors which are involved in the binding with the extra-cellular BAG3. The partners identified are involved in various biological processes such as membrane remodelling, apoptosis, and immune system development and modulation. In particular, the IFITM-2 receptor is involved in the apoptosis regulation processes, while NRP-1 plays a role in angiogenesis, thrombopoiesis, and the development of the cardiovascular system.

TABLE 1

Plasma membrane proteins co-purified in complex with rBAG3.

| Gene name | Access number |
|---|---|
| Adenylyl cyclase-associated protein 1 | P40124 |
| Clathrin heavy chain 1 | Q68FD5 |
| Constitutive coactivator of protein similar to PPAR gamma1 | Q6A0A9 |
| Glicoprotein-N-acetilgalattosamina3-betagalattosiltransferasi 1 | Q9JJ06 |
| D-D alpha chain, class I H2 histocompatibility antigen | P01900 |
| K-D alpha chain, class I H2 histocompatibility antigen | P01902 |
| Interferon 2-induced trans-membrane protein | Q99J93 |
| IIc low-affinity immunoglobulin receptor Fc region | P08101 |
| neuropilin 1 | P97333 |

Example 4. Negative Modulation of NRP-1 and -2 IFITM Levels in J774 Cells

J774 cells were seeded in a 24-well plate at 40% confluence, and after 24 hours transfected using specific siRNAs capable of negatively modulating NRP-1 and IFITM-2 levels. The siRNAs for NRP-1 and for IFITM2 were obtained from Santa Cruz (Santa Cruz, Calif., U.S.) and used for transfection with Transfectin (BIORAD, Carlsbad, U.S.) at a final concentration of 100 nM. After 72 hours, cells were harvested and lysed. The total proteins were then analyzed by separation in SDS-PAGE and the levels of the two receptors identified were then analyzed with Western blotting and hybridization with two specific antibodies. FIG. 3 shows a constitutive expression of both proteins and that siRNAs are able to modulate their expression negatively. An antibody capable of marking GAPDH protein was used to monitor identical gel loading conditions.

Example 5. Binding of the BAG3 Recombinant Protein to the J774 Cells Via the Surface Receptor J774 cells were transfected with specific siRNAs capable of negatively modulating the levels of NRP-1 or IFITM-2 or both, as described in Example 4. The NRP-1 and IFITM2 siRNAs were obtained from Santa Cruz (Santa Cruz, Calif., U.S.) and used for transfection with Transfectin (BIORAD, Carlsbad, U.S.) at a final concentration of 100 nM. After 48 hours, the cells were harvested, incubated with blocking buffer (PBS 1×/FBS 5%) for 30 minutes at 4° C. to which the BAG3 recombinant protein derivatized with FITC molecules (10 µg/million cells) was subsequently added for 30 minutes at 4° C. Subsequently, the cells were washed twice with PBS 1×/FBS 5%, centrifuged for 10 minutes at 1200 rpm, resuspended in PBS 1× and analyzed with flow cytometry. FIG. 4 shows that negative modulation of NRP-1, or IFITM-2, or both, brings with it a drastic decrease in the binding of the BAG3 recombinant protein to the cells. When the siRNAs used are capable of negatively modulating the levels of one of the two specific receptors identified, it results in an approximately 75% decrease in the binding; this decrease move to 88% when both proteins are muted.

This demonstrates that both the receptor chains participate in the binding with BAG3 and that it is sufficient to mute one of them to prevent the binding.

Example 6. Down-Modulation of NRP-1 and IFITM-2 Inhibiting Release of rBAG3-Induced Interleukin 6

J774 cells were seeded in 24-well plates at a confluence of 40%. After 24 hours, they were transfected with siRNAs for NRP-1, IFITM2, or both, at a final concentration of 100 nM. After 72 hours of muting, the rBAG3 protein (6 µg/ml) was added to the culture medium for 16 hours and 100 µl medium was collected for interleukin 6 assay via ELISA.

The rBAG3 protein activates the macrophages, thereby producing increased IL-6 release.

It can be observed in FIG. 5 that the effect on the BAG3-specific IL-6 secretion is drastically suppressed in the cells transfected with NRP-1- and IFITM-2-receptor-specific siRNAs. *** $p<0.001$ VS scrb.

This confirms that both receptor chains participate in the BAG3 action.

Example 7. Anti-IFITM-2 Antibody Preventing the Binding of rBAG3 to the Cell Surface of the J774 Cells It was then demonstrated that the binding of the rBAG3 protein can be inhibited through the use of molecules interposed between the BAG3 and the receptor thereof.

J774.A1 cells were resuspended in blocking solution (PBS/FBS 5%) at a density of 1 million/ml for 30 minutes at 4° C. The sample was then divided into three aliquots, incubated respectively with: A) BAG3-FITC (5 µg/million cells) for 30 minutes; B) Mouse IgG (150 µg/million cells) for 30 minutes and BAG3-FITC (5 µg/million cells) for a further 30 minutes; C) ab IFITM-2 (150 µg/million cells) (Novus Biologicals) for 30 minutes and BAG3-FITC (0.5 µg/ml) for a further 30 minutes. The cells were then washed twice with PBS/FBS 5%, centrifuged for 10 minutes at 1200 rpm, resuspended in 300 µl PBS and analyzed with flow cytometry.

As can be observed in FIG. 6, by occupying the sites of interaction between BAG3 and the IFITM-2 receptor using an IFITM-2-specific monoclonal antibody, a highly significant decrease in the binding of the BAG3 to the J774 cells is obtained.

IFITM2 constitutes a particularly useful target for therapy, because it enters the constitution of the receptor for BAG3 and does not enter that of other receptors containing NRP-1.

Example 8. Functional Characterization of Soluble BAG3 Protein

J774 cells were plated at a 60% confluence and incubated for 24 h with the BAG3 recombinant protein at concentrations of 10, 30, or 100 ng/ml. The nitrites production was verified in the culture medium using Griess reagent (1% sulphanilamide, 0.1% naphthyl ethylenediamine, 5% phosphoric acid) and measured using a Beckman DU-62 spectrophotometer at 550 nM.

The BAG3 recombinant protein was then used in macrophage activation assays in order to determine a possible role of the protein released in the serum in relation to the blood cells. To this end, the J774 murine monocyte cell line was treated with the BAG3 recombinant protein at different concentrations, using a pro-inflammatory agent, such as lipopolysaccharide (LPS), as a positive control. The activation of monocytes was measured by assay of nitrites. (FIG. 7).

The binding of the BAG3 protein to the cell surface of the J774 cells was then confirmed through conjugation of the recombinant protein with a fluorophore (FIG. 8). The BAG3 recombinant protein was then conjugated to FITC using the FluoroTag Conjugation FITC kit (SIGMA). Equal amounts of BSA-FITC (negative control) and rBAG3-FITC were added to the culture medium for 1 h. The cells were then fixed with a 3.7% formaldehyde solution and analyzed with a Zeiss LSM confocal microscope.

Example 9. BAG3 Secreted by Cardiac Myocytes Induced by Stress or by Pancreatic Tumour Cells Binding Specifically to the Surface of Macrophages Using BAG3 recombinant protein bound to fluorescein isothiocyanate (FITC), it was verified that BAG3 protein binds the surface of macrophages and not heart muscle cells (HCM) or pancreatic adenocarcinoma cells (PANC-1). (FIG. 9).

Confocal fluorescence microscopy analysis was performed to measure the binding of rBAG3-FITC to HCM, J774 A1, and PANC-1 cells. The BAG3 recombinant protein and the BSA (bovine serum albumin) (SIGMA) were conjugated to FITC using the FluoroTag Conjugation FITC kit (SIGMA) following the manufacturer's instructions. Equal amounts of rBAG3-FITC and BSA-FITC were added to the three cell lines in the presence of 0.1% NaN3 for 1 h. β-integrin protein was used as a positive control. Fluorescence was analyzed using a Zeiss LSM confocal microscope.

Example 10. FITC-BAG3 Bind the Macrophages of the J774 Cell Line

J774 A1 cells ($1\times10^6$ cells/ml) were incubated with different concentrations of BAG3 FITC protein (7, 14, and 70 nm). FITC-BSA (70 nM) was used as a negative control (grey). Fluorescence was analyzed by flow cytometry. (FIG. 10).

The BAG3 binding to macrophages can be specifically inhibited by BAG3-specific peptides or BAG3-specific F(ab')$_2$ antibodies (Table 2). In particular, J774 cells were incubated with 14 nM FITC-BAG3 protein and with 625 nM BAG3-specific peptides (peptide 1, peptide 2, peptide 3, peptide 4, or a scrambled peptide) or with 420 nM of anti-BAG3 F(ab') antibodies (mouse monoclonal antibodies AC1, AC2 and the polyclonal antibody produced in rabbit TOS2). Fragments F(ab') 2 of rabbit or mouse IgG were used as a negative control.

TABLE 2

| | FITC-rBAG3 positive cell % (±D.S.) | FITC-BSA positive cell % (±D.S.) | Competition assays positive cell % (±D.S.) | inhibition % |
|---|---|---|---|---|
| FITC-rBAG3 | 15.7 (±0.45) | | | |
| FITC-BSA | | 4.04 (±0.06) | | |
| (FITC-rBAG3)-(FITC-BSA) | 11.06 (±0.45) | | | |
| FITC-rBAG3 + Pep1 | | | 0.18 (±0.05) | 98.4 |
| FITC-rBAG3 + Pep2 | | | 1.21(±0.63) | 89.1 |
| FITC-rBAG3 + Pep3 | | | 5.86 (±0.43) | 47.2 |
| FITC-rBAG3 + Pep4 | | | 0.68 (±0.20) | 93.8 |
| FITC-rBAG3 + Pep Scr | | | 12.1 (±0.21) | 0.0 |
| FITC-rBAG3 + Mouse IgG F(ab')2 | | | 12.3 (±0.40) | 0.0 |
| FITC-rBAG3 + Rabbit IgG F(ab')2 | | | 14.7 (±0.20) | 0.0 |
| FITC-rBAG3 + AC1 IgG F(ab')2 | | | 4.11 (±0.26) | 62.8 |
| FITC-rBAG3 + AC2 IgG F(ab')2 | | | 3.76 (±0.43) | 66.0 |
| FITC-rBAG3 + TOS2 IgG F(ab')2 | | | 3.19 (±0.21) | 71.1 |

Example 11. Effect of rBAG3 on iNOS and COX-2 Expression

In order to explore the functional consequences of the binding of BAG3 to macrophages, we tested the effect of rBAG3 expression on inducible nitric oxide synthase (iNOS) and cyclo-oxygenase-2 (COX-2) in the cells. J774 cells at 80% confluence were incubated with a control medium, BSA, LPS or rBAG3 for 20 hours. Polymyxin was added to verify the presence of non-specific effects of endotoxins still present after the purification of the BAG3 recombinant protein. COX-2 and iNOS were analyzed in cell lysates by Western blotting.

Example 12. Analysis of Nitrite Release by J774 A1 Macrophages Incubated with rBAG3

J774 A1 cells at 80% confluence were incubated with a control medium, BSA, LPS, or rBAG3 for 24 hours. 100 pl supernatant from each sample was incubated with 100 pl Griess reagent; the optical density at 550 nm (OD550) was measured with a Beckman DU62 spectrophotometer. The nitrite concentration was assessed by comparing the sample's OD at 550 nm with that of a standard sodium nitrite curve (FIG. 12).

Example 13. Analysis of IL-6 Release by the J774 A1 Macrophages Incubated with rBAG3

J774A.1 cells at 80% confluence were incubated with a control medium, BSA, LPS, or BAG3 for 5 hours. IL-6 was measured in the cell culture medium using an ELISA test. IL-6 concentration was assessed by comparing the sample's ODs with that of a standard IL-6 recombinant curve (FIG. 13).

The invention claimed is:
1. A method for treating pancreatic cancer in a subject, comprising the step of administering to the subject a pharmaceutical composition comprising at least one BAG3 (Bcl2-associated athanogene 3) receptor-binding molecule that binds to IFITM-2 protein (interferon-induced transmembrane protein 2) and at least one pharmaceutically acceptable excipient, wherein said molecule is an antibody that binds IFITM-2 or an antigen-binding fragment thereof and inhibits the binding of BAG3 to the BAG3 receptor.

2. The method according to claim 1, wherein said antibody or antigen-binding fragment thereof is selected from the group consisting of: polyclonal antibodies, monoclonal antibodies, mouse antibodies, humanized antibodies, chimeric antibodies, recombinant antibodies, conjugated antibodies, scFv fragments, Fab fragments, and F(ab')$_2$ fragments.

3. The method according to claim 2, wherein said antibody is an anti-IFITM-2 antibody.

4. The method according to claim 1, wherein said subject is a human.

5. A method for treating pancreatic cancer, comprising the step of administering to the subject a BAG3 receptor-binding molecule that binds to IFITM-2 protein, wherein said molecule is an antibody that binds IFITM-2 or an antigen-binding fragment thereof and inhibits the binding of BAG3 to the BAG3 receptor.

6. The method according to claim 5, wherein said BAG3 receptor is expressed on the surface of macrophages.

7. The method according to claim 5, wherein said antibody or antigen-binding fragment thereof is selected from the group consisting of: polyclonal antibodies, monoclonal antibodies, mouse antibodies, humanized antibodies, chimeric antibodies, recombinant antibodies, conjugated antibodies, scFv fragments, Fab fragments, and F(ab')$_2$ fragments.

8. The method according to claim 5, wherein said antibody is an anti-IFITM-2 antibody.

9. The method according to claim 5, wherein said subject is a human.

10. A method of inhibiting the binding of BAG3 to macrophages, comprising the step of contacting macrophages with a BAG3 receptor-binding molecule that binds to IFITM-2 protein, wherein said molecule is an antibody or antigen-binding fragment thereof that binds IFITM-2 and inhibits the binding of BAG3 to the BAG3 receptor.

11. The method of claim 10, wherein said method is carried out in vitro.

12. The method of claim 10, wherein said method is carried out in vivo in a subject.

13. The method of claim 12, wherein said subject suffers from pancreatic cancer.

14. The method of claim 1, further comprising administering a pharmaceutical composition comprising at least one anti-BAG3 antibody and a pharmaceutically acceptable excipient.

15. The method of claim 14, wherein administering said pharmaceutical composition comprising an antibody that binds IFITM-2 or antigen-binding fragment thereof and a pharmaceutically acceptable excipient and administering said pharmaceutical composition comprising an anti-BAG3 antibody and a pharmaceutically acceptable excipient are simultaneous, separate, or sequential.

16. The method of claim 5, further comprising administering at least one anti-BAG3 antibody.

17. The method of claim 16, wherein administering said antibody that binds IFITM-2 or antigen-binding fragment thereof and administering said anti-BAG3 antibody are simultaneous, separate, or sequential.

* * * * *